United States Patent
Keenan et al.

(10) Patent No.: US 11,519,987 B2
(45) Date of Patent: Dec. 6, 2022

(54) MAGNETIC RESONANCE FINGERPRINTING THERMOMETRY

(71) Applicants: Case Western Reserve University, Cleveland, OH (US); Government of the United States, as represented by the Secretary of Commerce, Gaithersburg, MD (US); The Regents of the University of Colorado, a body corporate, Denver, CO (US)

(72) Inventors: Kathryn Keenan, Boulder, CO (US); Megan Poorman, Boulder, CO (US); Rasim Boyacioglu, Cleveland Heights, OH (US); Mark A. Griswold, Shaker Heights, OH (US)

(73) Assignees: Case Western Reserve University, Cleveland, OH (US); The Regents of the University of Colorado, Denver, CO (US); Government of the United States, As Represented by the Secretary of Commerce, Gaithersburg, MD (US)

(*) Notice: Subject to any disclaimer, the term of this patent is extended or adjusted under 35 U.S.C. 154(b) by 0 days.

(21) Appl. No.: 17/301,509

(22) Filed: Apr. 5, 2021

(65) Prior Publication Data
US 2021/0311146 A1    Oct. 7, 2021

Related U.S. Application Data

(60) Provisional application No. 63/004,660, filed on Apr. 3, 2020.

(51) Int. Cl.
*G01R 33/50*    (2006.01)
*G01R 33/56*    (2006.01)
(Continued)

(52) U.S. Cl.
CPC ............ *G01R 33/50* (2013.01); *A61B 5/0037* (2013.01); *A61B 5/055* (2013.01); *G01R 33/385* (2013.01); *G01R 33/5608* (2013.01)

(58) Field of Classification Search
CPC .. G01R 33/50; G01R 33/385; G01R 33/5608; A61B 5/055; A61B 5/0037
See application file for complete search history.

(56) References Cited

U.S. PATENT DOCUMENTS

| | | |
|---|---|---|
| 8,723,518 B2 | 5/2014 | Seiberlich |
| 2015/0301138 A1 | 10/2015 | Griswold |

(Continued)

OTHER PUBLICATIONS

Wang, Charlie Yi, et al. "Magnetic resonance fingerprinting with quadratic RF phase for measurement of T2* simultaneously with δf, T1, and T2" Magnetic Resonance in Medicine, vol. 81, No. 3, 2018, pp. 1849-1862., https://doi.org/10.1002/mrm.27543. (Year: 2018).*

(Continued)

*Primary Examiner* — Gregory H Curran
(74) *Attorney, Agent, or Firm* — Quarles & Brady LLP (57) ABSTRACT

A method for temperature quantification using magnetic resonance fingerprinting (MRF) includes acquiring MRF data from a region of interest in a subject using an MRF pulse sequence with smoothly varying RF phase for MR resonant frequencies that is played out continuously. For each of a plurality of time intervals during acquisition of the MRF data the method further includes comparing a set of the MRF data associated with the time interval to an MRF dictionary to determine at least one quantitative parameter of the acquired MRF data, determining a temperature change based on the at least one quantitative parameter and generating a quantitative map of the temperature change in the region of interest. The region of interest can include aqueous and adipose tissue.

12 Claims, 6 Drawing Sheets

(51) Int. Cl.
*A61B 5/055* (2006.01)
*A61B 5/00* (2006.01)
*G01R 33/385* (2006.01)

(56) References Cited

U.S. PATENT DOCUMENTS

2015/0301141 A1   10/2015   Griswold
2016/0033604 A1*   2/2016   Grodzki ............. G01R 33/5608
                                                              324/309

OTHER PUBLICATIONS

Ishihara Y, et al. A precise and fast temperature mapping use water proton chemical shift. Magnetic Resonance in Medicine 1995 34:814-823.

Ma D, et al. Magnetic resonance fingerprinting. Nature 2013 495:187-192.

McGivney, D., et al. "Towards continuous dictionary resolution in MR fingerprinting using a quadratic inner product model." Proceedings of the 25th Annual Meeting of ISMRM, Montréal, QC, Canada. vol. 27. 2019.

Odeen H et al. Non-lnvasive Thermometry with Magnetic Resonance Imaging. Theory and Applications of Heat Transfer in Humans, vol. 1, 2018.

Rieke, V. et al. "MR thermometry." J Magn Reson Imaging 27 (2008): 376-390.

Wang, C. Y., et al. "Magnetic resonance fingerprinting with quadratic RF phase for measurement of T2* simultaneously with df, T1, and T2." Magnetic resonance in medicine 81.3 (2019): 1849-1862.

Yang, M., et al. "Low rank approximation methods for MR fingerprinting with large scale dictionaries." Magnetic resonance in medicine 79.4 (2018): 2392-2400.

* cited by examiner

FIG. 6

MAGNETIC RESONANCE FINGERPRINTING THERMOMETRY

CROSS-REFERENCE TO RELATED APPLICATIONS

This application is based on, claims priority to, and incorporates herein by reference in its entirety U.S. Ser. No. 63/004,660 filed Apr. 3, 2020 and entitled "Magnetic Resonance Fingerprinting Thermometry."

FUNDING STATEMENT

This invention was made with government support under 70NANB18H006 awarded by the National Institute of Standards and Technology. The government has certain rights in the invention.

BACKGROUND

Magnetic resonance imaging (MRI) is a non-invasive imaging method that allows detailed pictures to be obtained within the human body. MM thermometry can be used to quantitatively map temperature changes within the body in near-real time for use in monitoring thermal surgical procedures. However, current MR thermometry methods are typically used to map temperature changes for aqueous tissues (water-based tissues) and can be difficult to use to map temperature changes quickly and accurately in adipose tissues (fat-based tissues).

Temperature monitoring in both adipose and aqueous tissues is important for guidance of thermal therapies in vivo. Conventional MR thermometry in aqueous tissues is based on the proton resonant frequency-shift (PRFS), which is a negative shift in the water molecule's proton resonant frequency with heating. This shift appears in the phase of a type of MRI image known as the gradient echo image. These images are able to be acquired in a few seconds, enabling near-real time mapping of temperature for aqueous tissues with MM. However, adipose tissues do not exhibit this shift in frequency due to the lack of free water protons, therefore, PRFS can be unreliable to map temperature changes in adipose tissues. To obtain temperature maps in adipose tissues, proton $T_1$ or $T_2$ relaxation mapping is typically employed. Relaxation techniques rely on changes in $T_1$ or $T_2$ to monitor changes in temperature. Magnetic relaxation of fat is known to be related to temperature changes. However, relaxation methods require accurate and precise mapping of $T_1$ and $T_2$, which can be difficult to achieve in the high temporal resolution (~3 s) required for guidance of therapies and on the time scale needed for near-real time imaging. Additionally, the relationship between relaxation and temperature must be calibrated prior to imaging. To obtain temperature contrast in both water and fat, recent methods combine PRFS with accelerated relaxation mapping. These methods, however, require the acquisition sequence and/or reconstruction to be modified to incorporate relaxation mapping which can slow the temporal resolution of the sequence and force compromises in mapping the relaxation.

Magnetic resonance fingerprinting (MRF) is a framework that enable quantitative mapping of multiple tissue properties simultaneously in any tissue type. Conventional MRF sequences have been developed that can map both relaxation and resonant frequency simultaneously. This is accomplished by combining a temporal acquisition with dictionary matching reconstructions based on modeling of all possible signal evolutions. However, conventional MRF requires at least 30 seconds of acquisition to reconstruct accurate property maps and is typically performed only once, not dynamically through time. Additionally, the sensitivity of MRF mapping changes in these properties has not been explored.

It would be desirable to provide a system and method for quantitative mapping of temperature changes in aqueous and adipose tissue using MRF that overcome the aforementioned drawbacks.

SUMMARY OF THE DISCLOSURE

In accordance with an embodiment, a method for temperature quantification using magnetic resonance fingerprinting (MRF) includes acquiring MRF data from a region of interest in a subject using an MRF pulse sequence with smoothly varying RF phase for MR resonant frequencies that is played out continuously. For each of a plurality of time intervals during acquisition of the MRF data the method further includes comparing a set of the MRF data associated with the time interval to an MRF dictionary to determine at least one quantitative parameter of the acquired MRF data, determining a temperature change based on the at least one quantitative parameter and generating a quantitative map of the temperature change in the region of interest.

In accordance with another embodiment, a magnetic resonance imaging (MRI) system includes a magnet system configured to generate a polarizing magnetic field about at least a portion of a subject, a magnetic gradient system including a plurality of magnetic gradient coils configured to apply at least one magnetic gradient field to the polarizing magnetic field, a radio frequency (RF) system configured to apply an RF field to the subject and to receive magnetic resonance signals from the subject using a coil array and a computer system. The computer system can be programmed to acquire MRF data from a region of interest in a subject using an MRF pulse sequence with smoothly varying RF phase for MR resonant frequencies that is played out continuously. For each of a plurality of time intervals during acquisition of the MRF data the computer system can be further programmed to compare a set of MRF data associated with the time interval to an MRF dictionary to determine at least one quantitative parameter of the acquired MRF data, determine a temperature change based on the at least one quantitative parameter, and generate a quantitative map of the temperature change in the region of interest.

In accordance with another embodiment, a method for temperature quantification using magnetic resonance fingerprinting (MRF) includes acquiring MRF data from a region of interest in a subject using an MRF pulse sequence with smoothly varying RF phase for MR resonant frequencies that is played out continuously. For each of a plurality of temperature measurement time intervals during acquisition of the MRF data the method further includes generating a thermal signal MRF dictionary, comparing a set of MRF data associated with the temperature measurement time interval to the thermal signal MRF dictionary to determine a temperature change, and generating a quantitative map of the temperature change in the region of interest.

In accordance with another embodiment, a magnetic resonance imaging (MRI) system includes a magnet system configured to generate a polarizing magnetic field about at least a portion of a subject, a magnetic gradient system including a plurality of magnetic gradient coils configured to apply at least one magnetic gradient field to the polarizing magnetic field, a radio frequency (RF) system configured to apply an RF field to the subject and to receive magnetic resonance signals from the subject using a coil array, and a computer system. The computer system can be programmed to acquire MRF data from a region of interest in a subject using an MRF pulse sequence with smoothly varying RF phase for MR resonant frequencies that is played out continuously. For each of a plurality of temperature measurement time intervals during acquisition of the MRF data the computer system can be further programmed to generate a thermal signal MRF dictionary, compare a set of MRF data associated with the temperature measurement time interval to the thermal signal MRF dictionary to determine a temperature change, and generate a quantitative map of the temperature change in the region of interest.

BRIEF DESCRIPTION OF THE DRAWINGS

The present invention will hereafter be described with reference to the accompanying drawings, wherein like reference numerals denote like elements.

DETAILED DESCRIPTION

Magnetic resonance fingerprinting ("MRF") is a technique that facilitates mapping of tissue or other material properties based on random or pseudorandom measurements of the subject or object being imaged. In particular, MRF can be conceptualized as evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE"), and sampling patterns, such as by modifying one or more readout encoding gradients. The acquisition parameters are varied in a random manner, pseudorandom manner, or other manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which as mentioned above may be random or pseudorandom, or may contain signals from different materials or tissues that are spatially incoherent, temporally incoherent, or both, MRF processes can be designed to map any of a wide variety of parameters. Examples of such parameters that can be mapped may include, but are not limited to, tissue parameters or properties such as longitudinal relaxation time ($T_1$), transverse relaxation time ($T_2$), and proton density (p), and device dependent parameters such as main or static magnetic field map ($B_0$). MRF is generally described in U.S. Pat. No. 8,723,518 and Published U.S. Patent Application No. 2015/0301141, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations which can include terms for the temperature dependence of the various terms. This comparison allows estimation of the physical properties, such as those mentioned above. As an example, the comparison of the acquired signals to a dictionary can be performed using any suitable matching or pattern recognition technique. The properties for the tissue or other material in a given voxel are estimated to be the values that provide the best signal match. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative properties, which can be extracted from the selected signal vector and used to generate the relevant quantitative property maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \qquad (1)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha,\phi)$ is a rotation due to RF differences; $R(G)$ is a rotation due to a magnetic field gradient; $T_1$ is a longitudinal, or spin-lattice, relaxation time; $T_2$ is a transverse, or spin-spin, relaxation time; D is diffusion relaxation; $E_i(T_1, T_2, D)$ is a signal decay due to relaxation differences; and $M_0$ is the magnetization in the default or natural alignment to which spins align when placed in the main magnetic field.

While $E_i(T_1, T_2, D)$ is provided as an example, in different situations, the decay term, $E_i(T_1, T_2, D)$, may also include additional terms, $E_i(T_1, T_2, D, \ldots)$ or may include fewer terms, such as by not including the diffusion relaxation, as $E_i(T_1, T_2)$ or $E_i(T_1, T_2, \ldots)$. Also, the summation on "j" could be replace by a product on "j". The dictionary may store signals described by, $$S_i = R_i E_i(S_{i-1}) \quad (2)$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

Thus, in MRF, a unique signal timecourse is generated for each pixel. This timecourse evolves based on both physiological tissue properties such as T1 or T2 as well as acquisition parameters like flip angle (FA) and repetition time (TR). This signal timecourse can, thus, be referred to as a signal evolution and each pixel can be matched to an entry in the dictionary, which is a collection of possible signal evolutions or timecourses calculated using a range of possible tissue property values and knowledge of the quantum physics that govern the signal evolution. Upon matching the measured signal evolution/timecourse to a specific dictionary entry, the tissue properties corresponding to that dictionary entry can be identified. A fundamental criterion in MRF is that spatial incoherence be maintained to help separate signals that are mixed due to undersampling. In other words, signals from various locations should differ from each other, in order to be able to separate them when aliased.

Figure 1:
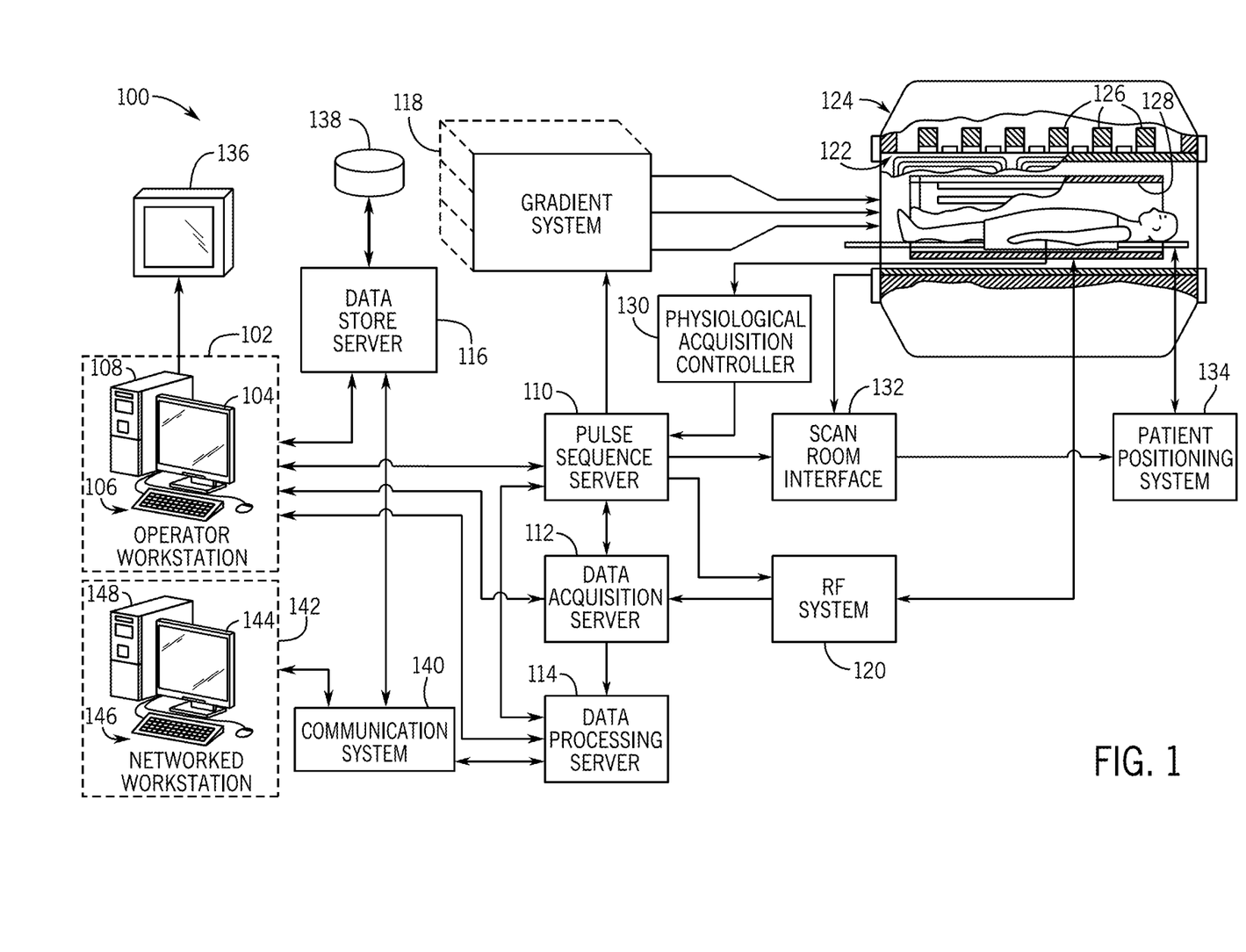
FIG. 1 is a schematic diagram of an example MRI system in accordance with an embodiment.

To achieve this process, a magnetic resonance imaging (MRI) system or nuclear magnetic resonance (NMR) system may be utilized. FIG. 1 shows an example of an MM system 100 that may be used to perform magnetic resonance fingerprinting. In addition, MRI system 100 may be used to implement the methods described herein. MRI system 100 includes an operator workstation 102, which may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MM system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MM pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (3);$$

and the phase of the received magnetic resonance signal may also be determined according to the following relationship:

$$\varphi = \tan^{-1}\left(\frac{Q}{I}\right). \quad (4)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MM system 100 may also include one or more networked workstations 142. For example, a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The present disclosure describes systems and methods for temperature quantification using magnetic resonance fingerprinting (MRF). The described systems and methods may be used for multi-contrast temperature mapping of aqueous and adipose tissues. The temperature quantification systems and methods can leverage multiple MRI contrast pathways to accurately map changes in temperature in tissues. In some embodiments, the systems and methods can be used to determine temperature changes in aqueous and adipose tissue simultaneously. The systems and methods for temperature quantification using MRF can utilize an MRF pulse sequence with smoothly varying RF phase for RF resonant frequencies played out continuously during an acquisition of MRF data. In some embodiments, the MRF pulse sequence is an MRF with quadratic RF phase (MRFqRF) pulse sequence although it should be understood that other sweep patterns that provide an RF phase that changes smoothly in time (or smoothly varying RF phase) may be used with the systems and methods described herein. In some embodiments, temperature changes may be determined at a plurality of predetermined time intervals during an acquisition (or scan) using the MRF pulse sequence with smoothly varying RF phase for RF resonant frequencies played out continuously. In an embodiment, at each predetermined time interval, one or more parameters (e.g., tissue properties or parameters such as $T_1$ or $T_2$, or device dependent parameters such as $B_0$) of the acquired MR data for a region of interest in a subject may be determined and the one or more parameters can be converted to temperature (e.g., $\Delta T$) for a tissue or tissues in the region of interest. In another embodiment, at each predetermined time interval, the temperature (e.g., $\Delta T$) of a tissue or tissues in the region of interest in the subject may be determined directly by matching the acquired MR data from the region of interest to a thermal signal MRF dictionary. The thermal signal MRF dictionary may be updated dynamically at each predetermined time interval during the acquisition (or scan) using, for example, information (e.g., the magnetization) from a previous time interval. Accordingly, in some embodiments the thermal signal MRF dictionary may be advantageously created and updated on the fly during an acquisition.

In some embodiments, the systems and methods for temperature quantification using MRF may be used to continuously monitor the temperature of tissues in a subject during thermal surgical procedures and guidance of thermal therapies that include the application of heating or cooling to tissues in a subject (e.g., procedures or therapies performed with a laser ablation system, other systems for heating tissue or other systems for cooling tissues). In an embodiment, the MRF temperature quantification systems and methods may be used to determine temperature changes due to heating of one or more tissues (e.g., aqueous or adipose tissues) in a region of interest in a subject. In another embodiment, the MRF temperature quantification systems and methods may be used to determine temperature changes due to cooling of one or more tissues (e.g., aqueous or adipose tissues) in a region of interest in a subject. Further advantages of the described systems and methods are that no interleaving is required and the systems and methods may be used in low signal-to-noise ratio (SNR) scenarios.

Figure 2:
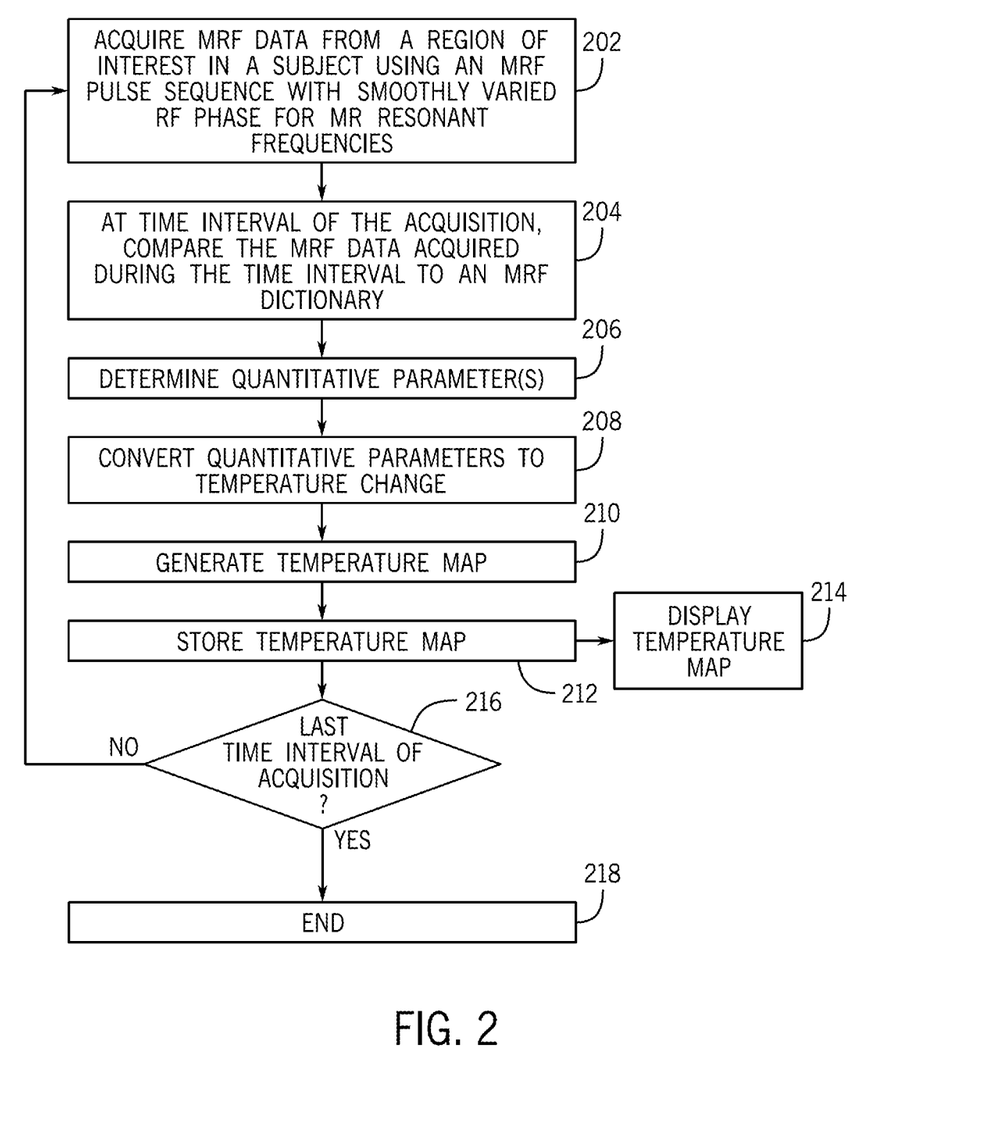
FIG. 2 illustrates a method for magnetic resonance fingerprinting (MRF) thermometry in accordance with an embodiment.
Figure 3:
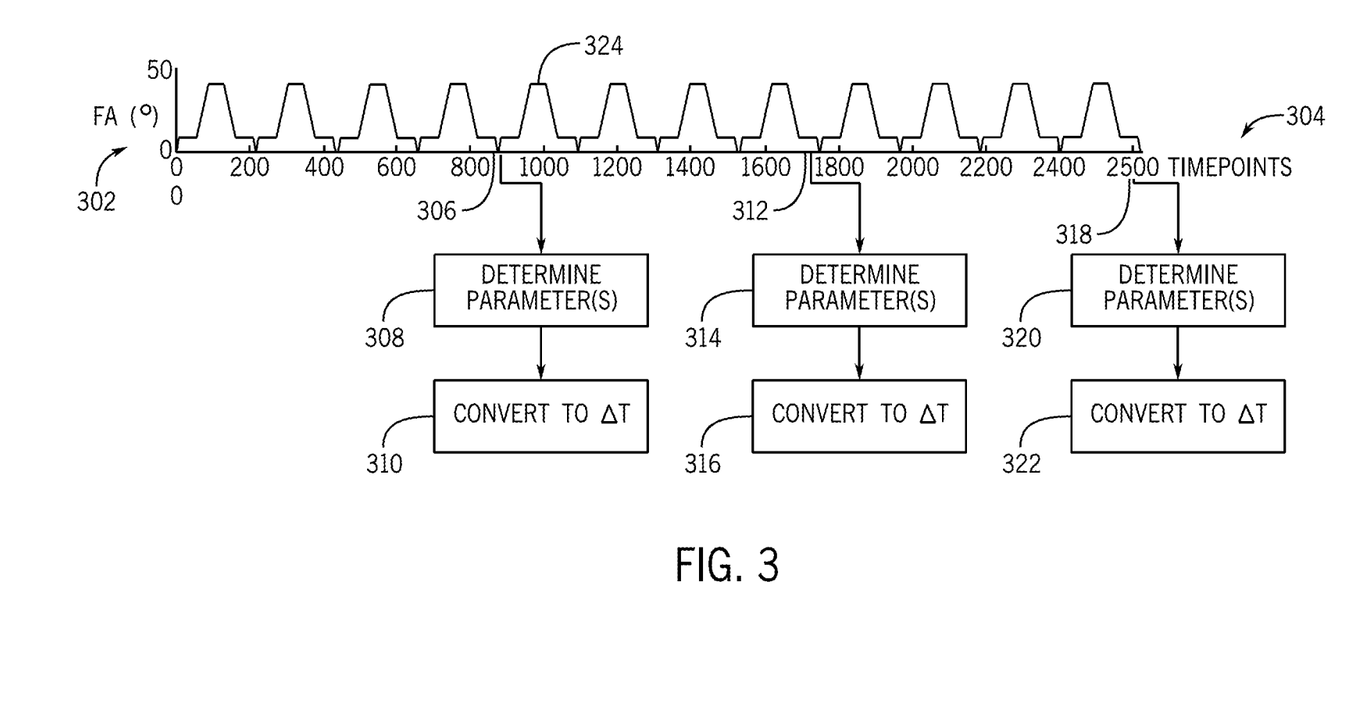
FIG. 3 illustrates an example flip angle pattern and time intervals for determining temperature changes using the method of FIG. 2 in accordance with an embodiment.

FIG. 2 illustrates a method for magnetic resonance fingerprinting (MRF) thermometry in accordance with an embodiment and FIG. 3 illustrates an example flip angle pattern and time intervals for determining temperature changes using the method of FIG. 2 in accordance with an embodiment. The method for MRF thermometry may be used for temperature quantification and multi-contrast temperature mapping. At block 202, MRF data may be acquired from tissue (e.g., aqueous and/or adipose tissue) in region of interest in a subject using, for example, an MM system (e.g., MM system 100 shown in FIG. 1). The MRF data can be acquired by the MRI system using an MRF pulse sequence with a smoothly varying RF phase for MRF resonant frequencies played out continuously during the acquisition or scan. In an embodiment the MRF pulse sequence with smoothly varying RF phase can be optimized to provide a faster temporal resolution for the temperature quantification and monitoring. For example, the number of time points per scan can be reduced which results in an increase in temporal resolution, a faster acquisition and increase sensitivity to $B_0$ or resonant frequency changes. In addition, a decrease in the number of time points can result in reduced signal to noise ratio (SNR). Reduction of the number of time points can bring finer resolution sampling of the temperature curves through time. In various embodiments, the MRF pulse sequence may be configured to be sensitive to one or more parameters such as $T_1$, $T_2$, $T_2^*$, $B_0$ and off-resonance ($\Delta f$). In some embodiments, the $T_1$ sensitivity of the MRF pulse sequence may be increased by periodically applying an inversion RF pulse during the acquisition.

In some embodiments, the MRF pulse sequence is a MRF with quadratic RF phase (MRFqRF) pulse sequence. While the following description will be discussed in terms of embodiments using an MRFqRF sequence and quadratic RF phase, it should be understood that in other embodiments other sweep patterns that provide an RF phase that changes smoothly in time (or smoothly varying RF phase) may be used in the systems and methods described herein to acquire the MRF data. An MRFqRF pulse sequence may be used to simultaneously quantify $T_1$, $T_2$, $T_2^*$, $B_0$ and off-resonance ($\Delta f$). An MRFqRF pulse sequence can be configured to, for example, sweep the on-resonance frequency linearly between $-1/(2*TR)$ to $1/(2*TR)$ in time by modulating the RF phase with a quadratic function. In some embodiments, a larger or smaller range for the sweep of the on-resonance frequency may be used. As mentioned above, in an embodiment the MRFqRF sequence can be optimized to provide a faster temporal resolution for the temperature quantification and monitoring. For example, the number of time points per acquisition using the MRFqRF pulse sequence can be reduced (compared to a conventional MRFqRF acquisition) to provide a faster temporal resolution for the temperature quantification. An example MRFqRF flip angle sweep pattern is shown in FIG. 3. In FIG. 3, a flip angle pattern 324 representing flip angles 302 over time (e.g., time points 304) is shown.

As the acquisition at block 202 of FIG. 2 is played out, temperature changes are determined at a plurality of predetermined time intervals during an acquisition as shown in FIG. 3. In the embodiment shown in FIG. 3, three time intervals 306, 312 and 318 are shown, however, it should be understood that an acquisition according to the disclosed temperature quantification method can include more than three time intervals. The time interval at which the temperature changes are determined may be defined in terms of, for example, a number of time points or seconds of acquisition time. Each time interval can represent a separate continuous dynamic scan. In the example shown in FIG. 3, the MRFqRF scan can be implemented with time intervals 306, 312, 318 that each include 876 time points. In this example, a time interval 306, 312, 318 with 876 time points may correspond to approximately 9.6 seconds of acquisition time. Accordingly, a temperature change may be measured approximately every 9.6 seconds during the MRFqRF acquisition of block 202. In addition, in the example of FIG. 3, the off-resonance frequencies may be swept 2.88 Hz/TR by applying quadratic phase to the RF pulses. While the example shown in FIG. 3 illustrates 876 time points per time interval, it should be understood that the time intervals may include other numbers of time points. As mentioned above, the number of time points are configured to provide a sufficient temporal resolution for temperature quantification and monitoring. As shown in FIG. 3, temperature of one or more tissues is determined at each time interval 306, 312, 318 by determining quantitative properties or parameters (e.g., $T_1$, $T_2$, $B_0$) 308, 314, 320, respectively and converting 310, 316, 322, respectively, the determined properties or parameters to a change in temperature ($\Delta T$).

Returning to FIG. 2, at block 204, at the predetermined time interval (e.g., time interval 306) the MRF data acquired during the time interval is compared to an MRF dictionary. The MRF dictionary includes known signal evolutions (e.g., simulated signal evolutions). In an embodiment, the MRF dictionary may be generated using a Bloch simulation. Each entry (or signal evolution) in the MRF dictionary corresponds with a set of quantitative parameters, for example, tissue properties or parameters such as $T_1$, $T_2$, and proton density, and device dependent parameters such as $B_0$. The MRF dictionary may be stored in and retrieved from memory or data storage of, for example, the MM system 100 shown in FIG. 1) or other computer system. In an embodiment, the MRF dictionary may be a compressed MRF dictionary. For example, the MRF dictionary may be compressed using a known compression method such as, for example, singular value decomposition (SVD) or randomized SVD (rSVD). In an embodiment, the compressed MRF dictionary may also be partially undersampled in the tissue dimension. The low resolution in the tissue dimension may be recovered with quadrative interpolation after comparison and matching. In an embodiment, the acquired MRF data may also be compressed using a known compression method such as, for example, rSVD.

In some embodiments, the MRF data may be reconstructed before comparison with the MRF dictionary using known methods (e.g., a non-uniform Fast Fourier Transform (NUFFT)). In an embodiment, Independent Component Analysis (ICA) may be used on the MRF data or reconstructed images) to detect and estimate frequency drift. A component that describes the linear frequency drift may then be removed from all voxels in the MRF data (or reconstructed images). The MRF data and/or reconstructed images may be stored in memory or data storage of, for example, the MRI system 100 shown in FIG. 1) or other computer system. The MRF data (or reconstructed images) are compared to the MRF dictionary at block 204 to match the MRF data with the signal evolutions stored in the MRF dictionary. "Match" as used herein refers to the result of comparing signals but does not refer to an exact match, which may or may not be found. A match may be the signal evolution that most closely resembles another signal evolution. Comparing the MRF data (or reconstructed images) to the MRF dictionary may be performed in a number of ways such as, for example, using a pattern matching, template matching, or other matching algorithm, including the use of non-linear fitting, or the use of deep learning or neural network structures.

At block 206, one or more quantitative parameters of the MRF data acquired during the time interval are determined based on the comparison and matching at block 204 to identify matching dictionary entry or entries (i.e., matching signal evolution(s)). In one embodiment, the determined quantitative parameters may include $T_1$, $T_2$, $B_0$, and off-resonance ($\Delta f$). In an embodiment, a quantitative map may be generated for each identified quantitative parameter. The identified quantitative parameters may be stored in memory or data storage of, for example, the MRI system 100 shown in FIG. 1) or other computer system. At block 208, the one or more quantitative parameters identified at block 208 may be converted to a temperature change ($\Delta T$) using known methods. In one embodiment, one of the determined quantitative parameters may be off-resonance (Δf). Residual changes in off-resonance may be used to predict the temperature changes. In an example, the following equation may be used to convert the off-resonance (Δf) to temperature (ΔT):

$$\Delta T_n = \frac{\Delta f_n - \Delta f_0}{-0.01 * \gamma * B_0} \quad (5)$$

where γ is the gyromagnetic ratio in MHz/T, $B_0$ is the field strength in Tesla, and n is the dynamic scan number. At block 210, a temperature map may be generated indicating the temperature change determined at block 208. For example, a map may be generated having a quantitative indication of the determined temperature. At block 212, the temperature map may be stored in memory or data storage of, for example, the MRI system 100 shown in FIG. 1) or other computer system. In an embodiment, the temperature map may also be provided to and displayed on a display (e.g., display 104, 1356 or 144 of MRI system 100 shown in FIG. 1) at block 214.

At block 216, it is determined whether there are any additional time intervals in the acquisition for which a temperature changes may be determined or if the acquisition is complete. If there is an additional time interval, the process returns to block 204 and the MRF data from the next time interval (e.g., time interval 312 shown in FIG. 3) is compared to the MRF dictionary. Blocks 204-214 are performed for each time interval to determine a temperature change at the corresponding point in time of the acquisition. Accordingly, blocks 204-214 may be repeated dynamically. As shown in FIG. 3, at a first time interval 306, quantitative parameters are determined 308 based on the MRF data acquired during the interval 306 and the identified parameters are converted to temperature change 310. At a second time interval 312, quantitative parameters are determined 314 based on the MRF data acquired during the interval 312 and the identified parameters are converted to temperature change 316. At a third time interval 318, quantitative parameters are determined 320 based on the MRF data acquired during the interval 318 and the identified parameters are converted to temperature change 322. In the embodiment shown in FIG. 3, quantitative parameters may be determined for every 876 time points (approximately 9.6 seconds of MRF data) by matching the acquired MRF data in the corresponding time interval to the MRF dictionary and the determined quantitative parameters are converted to temperature (ΔT). Accordingly, in some embodiments a temperature map may be generated approximately every 9.6 seconds.

Returning to FIG. 2, at block 216 if there are no remaining time intervals and the acquisition is complete, the process ends at block 218. As mentioned above, in some embodiments the method for temperature quantification using MRF may be used to monitor the temperature of tissues in a subject during thermal surgical procedures and guidance of thermal therapies. In such embodiments, the total length of the MRF acquisition (e.g., an MRFqRF acquisition as described above) may be determined based on the duration of the heating or cooling of the subject during the thermal surgical procedure or thermal therapy. In some embodiments, the thermal procedure, therapy or treatment may be stopped (manually or automatically) based on the determined temperature change and temperature map (blocks 208 and 210), for example, if the determined temperature falls above or below a predetermined threshold. In some embodiments, the thermal therapy or treatment may be modified (manually or automatically) based on the determined temperature change and temperature map (blocks 208 and 210), for example, if the determined temperature falls above or below a predetermined threshold.

Figure 4:
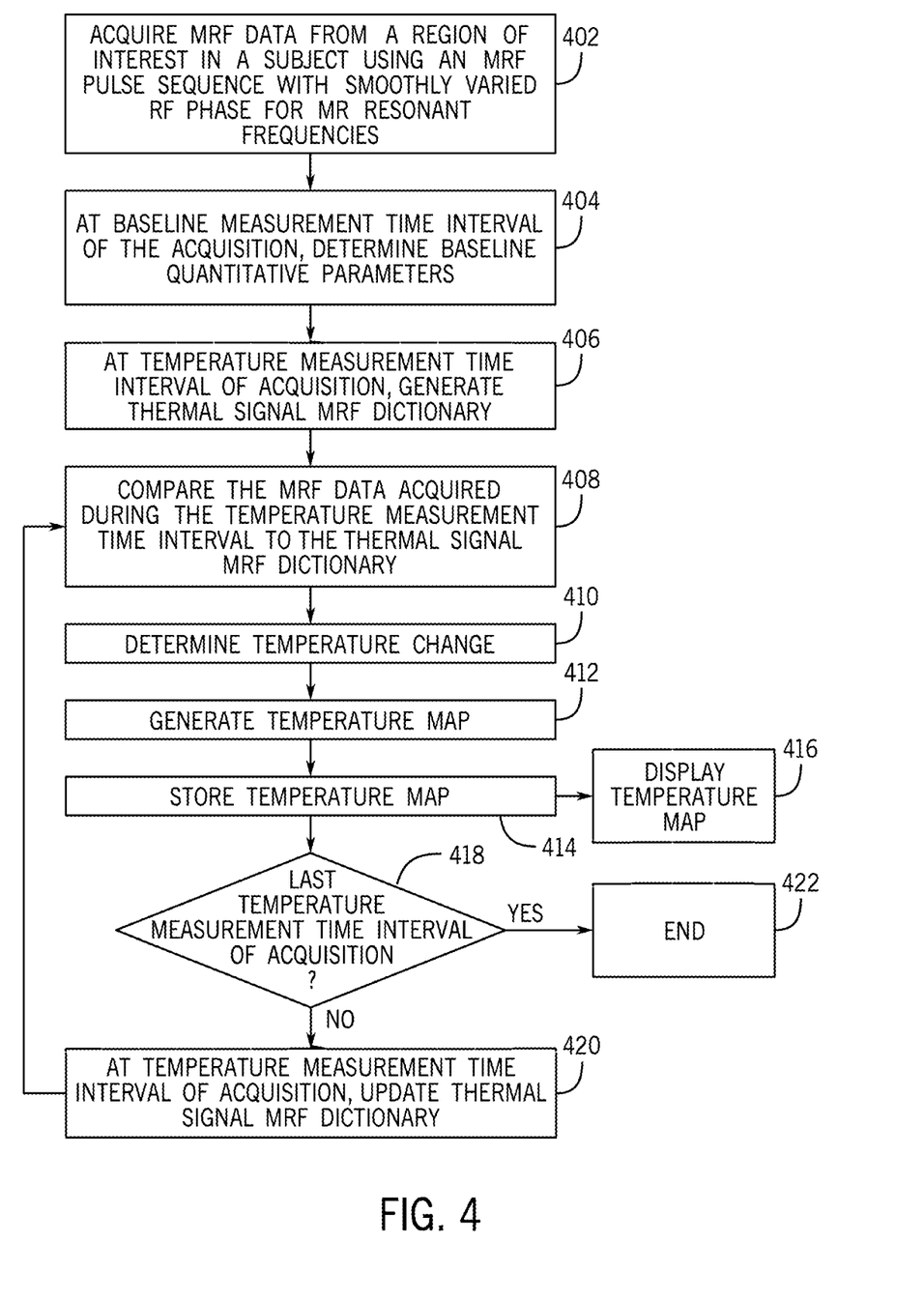
FIG. 4 illustrates a method for magnetic resonance fingerprinting (MRF) thermometry using a thermal MRF dictionary in accordance with an embodiment.
Figure 5:
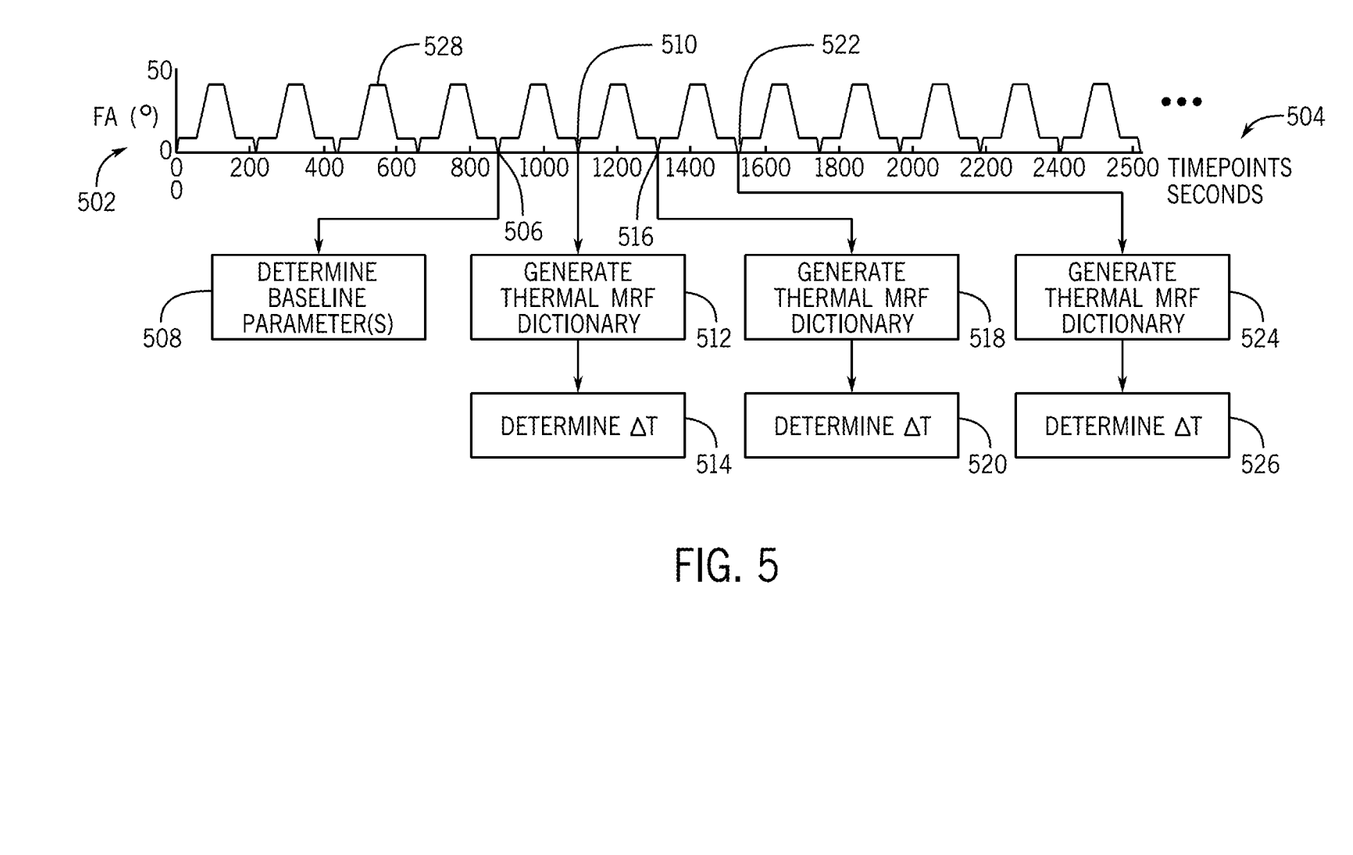
FIG. 5 illustrates an example flip angle pattern and time intervals for determining temperature changes using the method of FIG. 4 in accordance with an embodiment.

In some embodiments, it may be desirable to further increase the temporal resolution for clinical applications and to, for example, improve temperature measurements for adipose tissues. To further increase the temporal resolution, at each predetermined time interval, the temperature (e.g., ΔT) of a tissue or tissues in the region of interest in the subject may be determined directly by matching the acquired MR data from the region of interest to a thermal signal MRF dictionary. FIG. 4 illustrates a method for magnetic resonance fingerprinting (MRF) thermometry using a thermal MRF dictionary in accordance with an embodiment and FIG. 5 illustrates an example flip angle pattern and time intervals for determining temperature changes using the method of FIG. 4 in accordance with an embodiment. At block 402, MRF data may be acquired from a tissue (e.g., aqueous and/or adipose tissue) in region of interest in a subject using, for example, an MRI system (e.g., MRI system 100 shown in FIG. 1). The MRF data can be acquired by the MRI system using an MRF pulse sequence with smoothly varied RF phase for MRF resonant frequencies played out continuously during the acquisition or scan. As discussed above with respect to block 202 of FIG. 2, in an embodiment the MRF pulse sequence with smoothly varying RF phase can be optimized to provide a faster temporal resolution for the temperature quantification and monitoring. For example, the number of time points per scan can be reduced which results in an increase in temporal resolution, a faster acquisition and increase sensitivity to $B_0$ or resonant frequency changes. In addition, a decrease in the number of time points can result in reduced signal to noise ratio (SNR). Reduction of the number of time points can bring finer resolution sampling of the temperature curves through time. In various embodiments, the MRF pulse sequence may be configured to be sensitive to one or more parameters such as $T_1$, $T_2$, $T_2^*$, $B_0$ and off-resonance (Δf). In some embodiments, the $T_1$ sensitivity of the MRF pulse sequence may be increased by periodically applying an inversion RF pulse during the acquisition.

In some embodiments, the MRF pulse sequence is a MRF with quadratic RF phase (MRFqRF) pulse sequence as discussed above. While the following description will be discussed in terms of embodiments using an MRFqRF sequence and quadratic RF phase, it should be understood that in other embodiments other sweep patterns that provide a phase that changes smoothly in time (or smoothly varying phase) may be used in the systems and methods described herein to acquire the MRF data. As discussed above with respect to FIG. 2, the MRFqRF pulse sequence can be optimized to provide a faster temporal resolution for the temperature quantification and monitoring. For example, the number of time points per acquisition using the MRFqRF pulse sequence can be reduced (compared to a conventional MRFqRF acquisition) to provide a faster temporal resolution for the temperature quantification. An example MRFqRF flip angle sweep pattern is shown in FIG. 5. In FIG. 5, a flip angle pattern 528 representing flip angles 502 over time (e.g., time points 504) is shown.

As the acquisition at block 402 of FIG. 4 is played out, a baseline measurement is made at a predetermined baseline measurement time interval and then temperature changes are determined at a plurality of predetermined temperature measurement time intervals during an acquisition as shown in FIG. 5. In the embodiment shown in FIG. 5, one baseline measurement time interval 506 and three temperature measurement time intervals 510, 516 and 522 (or "dynamics") are shown. However, it should be understood that an acquisition according to the disclosed temperature quantification method can include more than three temperature measurement time intervals. The baseline measurement time interval and the time measurement time intervals may be defined in terms of, for example, a number of time points or seconds of acquisition time. Each temperature measurement time interval can represent a separate continuous dynamic scan. In the example shown in FIG. 5, the baseline measurement time interval 506 contains 876 time points which may correspond to, for example, approximately 9.6 seconds of acquisition time. In addition, the MRFqRF scan can be implemented with temperature change time intervals 510, 516, 522 that each include 219 time points. In this example, a time measurement time interval 510, 516, 522 with 219 time points may correspond to approximately 2.6 seconds of acquisition time. Accordingly, a temperature change may be measured every 219 time points or approximately every 2.6 seconds during the MRFqRF acquisition of block 402. In addition, in the example of FIG. 5, the off-resonance frequencies may be swept 2.88 Hz/TR by applying quadratic phase to the RF pulses. While the example shown in FIG. 5 illustrates 876 time points for the baseline measurement time interval and 219 time points per time measurement time interval, it should be understood that the time intervals may include other numbers of time points. As mentioned above, the number of time points are configured to provide a sufficient temporal resolution for temperature quantification and monitoring. As shown in FIG. 5, temperature of one or more tissues is determined at each temperature measurement time interval 510, 516, 522 by generating a thermal signal MRF dictionary 512, 518, 524, respectively and determining temperature ($\Delta T$) 514, 520, 526, respectively. As described further below, the temperature change at each temperature measurement time interval may be determined directly by comparing the MRF data for the particular time interval to a thermal signal MRF dictionary.

Returning to FIG. 4, baseline values for quantitative parameters such as, for example, $T_1$, $T_2$ and $B_0$ are determined at block 404. In an embodiment where the disclosed method is used for monitoring a thermal surgical procedure or thermal therapy, the baseline quantitative parameters may be determined before heating or cooling is applied to tissue of the subject. At the predetermined baseline measurement time interval (e.g., interval 506 shown in FIG. 5), the baseline quantitative parameters can be determined by comparing the MRF data acquired during the baseline measurement time interval to an MRF dictionary. As described above with respect to block 204 of FIG. 2, the MRF dictionary can include known signal evolutions (e.g., simulated signal evolutions generated using a Bloch simulation). Each entry (or signal evolution) in the MRF dictionary corresponds with a set of quantitative parameters, for example, tissue properties or parameters such as $T_1$, $T_2$, and proton density, and device dependent parameters such as $B_0$. The MRF dictionary may be stored in and retrieved from memory or data storage of, for example, the MRI system 100 shown in FIG. 1) or other computer system. In an embodiment, the MRF dictionary may be a compressed MRF dictionary. For example, the MRF dictionary may be compressed using a known compression method such as, for example, singular value decomposition (SVD) or randomized SVD (rSVD). In an embodiment, the compressed MRF dictionary may also be partially undersampled in the tissue dimension. The low resolution in the tissue dimension may be recovered with quadrative interpolation after comparison and matching. In an embodiment, the acquired MRF data may also be compressed using a known compression method such as, for example, rSVD.

In some embodiments, the MRF data may be reconstructed before comparison with the MRF dictionary using known methods (e.g., a non-uniform Fast Fourier Transform (NUFFT)). In an embodiment, Independent Component Analysis (ICA) may be used on the MRF data or reconstructed images) to detect and estimate frequency drift. A component that describes the linear frequency drift may then be removed from all voxels in the MRF data (or reconstructed images). The MRF data and/or reconstructed images may be stored in memory or data storage of, for example, the MRI system 100 shown in FIG. 1) or other computer system. The MRF data (or reconstructed images) are compared to the MRF dictionary at block 404 to match the MRF data with the signal evolutions stored in the MRF dictionary as discussed above. Comparing the MRF data (or reconstructed images) to the MRF dictionary may be performed in a number of ways such as, for example, using a pattern matching, template matching, or other matching algorithm, including the use of non-linear fitting, or the use of deep learning or neural network structures. In some embodiments, the baseline quantitative parameters determined at block 404 include, but are not limited to, $T_1$, $T_2$ and $B_0$. In an embodiment, a quantitative map may be generated for each determined baseline quantitative parameter identified. The identified baseline quantitative parameters may be stored in memory or data storage of, for example, the MM system 100 shown in FIG. 1) or other computer system.

Figure 6:
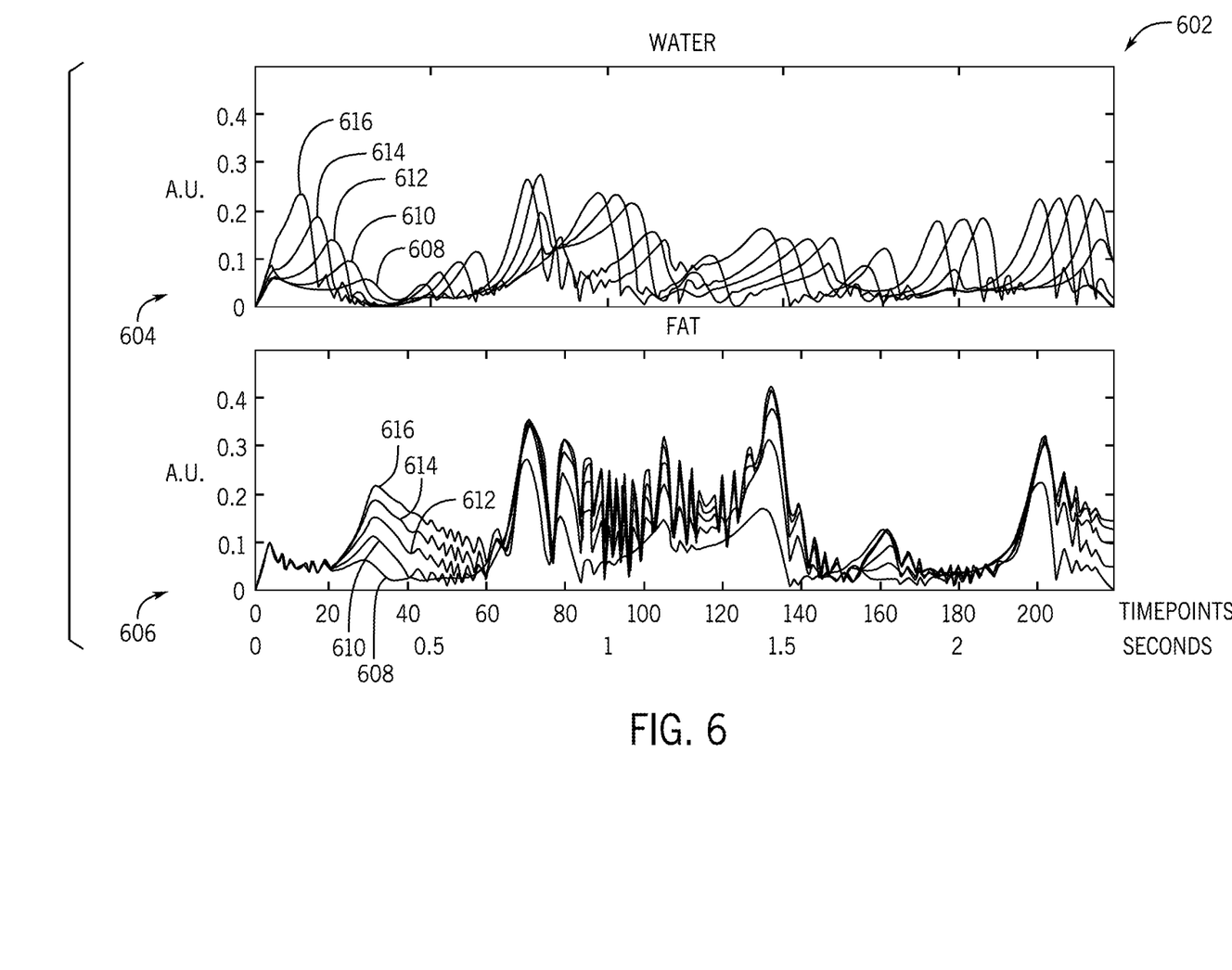
FIG. 6 illustrates example thermal signal MRF dictionary entries in accordance with an embodiment.

At block 406, at the predetermined temperature measurement time interval (e.g., interval 510 shown in FIG. 5), a thermal signal MRF dictionary is generated. The generated thermal signal MRF dictionary may be stored in memory or data storage of, for example, the MM system 100 shown in FIG. 1) or other computer system. The thermal signal MRF dictionary includes signal evolutions based on changes in temperature and may be generated using the baseline parameters determined at block 404 and known relationships between the parameters (e.g., relaxation, resonant frequency) and temperature. In an embodiment, the thermal signal MRF dictionary may be generated using Bloch simulations (which can include terms for the temperature dependence of the various terms) for a range of temperature steps from baseline. Accordingly, the baseline parameters (and magnetization) determined from the baseline measurement time interval may be used as input for the simulations. In some embodiments, the thermal signal MRF dictionary includes signal evolutions for both aqueous and adipose tissues, allowing the temperature to be fit directly regardless of tissue type. FIG. 6 illustrates example thermal signal MRF dictionary entries in accordance with an embodiment. In FIG. 6, signal evolutions for water 604 and fat 606 are shown for a range of temperature steps. Each signal evolution for water 604 and fat 606 corresponds to a temperature step, namely, $\Delta T=0$ (curve 608), $\Delta T=10$ (curve 610), $\Delta T=20$ (curve 612), $\Delta T=30$ (curve 614), and $\Delta T=40$ (curve 616). In the example dictionary entries of FIG. 6, frequency, $T_1$, and $T_2$, may be updated according to the following linear equations using known constants for both water and fat:

$$df_n = df_{n-1} + \alpha \gamma B_0 \Delta T \tag{6}$$

$$T1_n = T1_{n-1} + \beta \Delta T \tag{7}$$

$$T2_n = T2_{n-1} + \varphi \Delta T \tag{8}$$

In the example shown in FIG. 6, for water 604 the dictionary peaks change eft to right due to changes in $B_0$ and for fat 606 the peaks shift from left to right in relative magnitude due to changes in $T_1$ and $T_2$. Combining both water 604 and fat 606 in the dictionary enables direct fitting for temperature for both types of tissues (aqueous and adipose) simultaneously.

Returning to FIG. 4, at block 408 at the temperature measurement time interval (e.g., interval 510 shown in FIG. 5), the MRF data acquired during the temperature measurement time interval is compared to the thermal signal MRF dictionary generated at block 406. In an embodiment, the MRF data acquired in the temperature measurement time interval may be concatenated with the baseline data acquired during the baseline measurement time interval before comparison to the thermal signal MRF dictionary. In some embodiments, the MRF data may be reconstructed before comparison with the thermal signal MRF dictionary using known methods (e.g., a non-uniform Fast Fourier Transform (NUFFT)). The MRF data and/or reconstructed images may be stored in memory or data storage of, for example, the MRI system 100 shown in FIG. 1) or other computer system. The MRF data (or reconstructed images) are compared to the thermal signal MRF dictionary at block 408 to match the MRF data acquired during the temperature measurement time interval with the signal evolutions stored in the thermal signal MRF dictionary. Comparing the MRF data (or reconstructed images) to the thermal signal MRF dictionary may be performed in a number of ways such as, for example, using a pattern matching, template matching, or other matching algorithm, including the use of non-linear fitting, or the use of deep learning or neural network structures. In an embodiment, the comparison of the acquired MRF data to the thermal signal MRF dictionary includes matching acquired MRF data from each voxel to the thermal signal MRF dictionary.

At block 410, a temperature change for the MRF data is determined based on the comparison and matching at block 408 to identify matching dictionary entry or entries (i.e., matching signal evolution(s)). The identified temperature change may be stored in memory or data storage of, for example, the MM system 100 shown in FIG. 1) or other computer system. At block 412, a temperature map may be generated indicating the temperature change determined at block 410. For example, a map may be generated having a quantitative indication of the determined temperature. At block 414, the temperature map may be stored in memory or data storage of, for example, the MM system 100 shown in FIG. 1) or other computer system. In an embodiment, the temperature map may be provided to and displayed on a display (e.g., display 104, 1356 or 144 of MRI system 100 shown in FIG. 1) at block 416.

At block 418, it is determined whether there are any additional temperature measurement time intervals in the acquisition for which a temperature change may be determined or if the acquisition is complete. If there is an additional temperature measurement time interval, an updated thermal signal MRF dictionary is generated at block 420 for the next temperature measurement time interval (e.g., time interval 516 shown in FIG. 5). The updated thermal signal MRF dictionary includes signal evolutions based on changes in temperature and may be generated using the magnetization (e.g., the matched signal evolution and associated parameters such as temperature) from the prior temperature measurement time interval (e.g. the prior dynamic) and known relationships between the parameters (e.g., relaxation, resonant frequency) and temperature. For example, the thermal signal MRF dictionary may be generated using Bloch simulations for a range of temperature steps from baseline and the magnetization determined from the prior time measurement time interval may be used as input for the simulations.

The process then returns to block 408 and the MRF data from the next temperature measurement time interval (e.g., time interval 516 shown in FIG. 5) is compared to the updated thermal signal MRF dictionary from block 420. Blocks 408-420 are performed at each time measurement time interval to update the thermal signal MRF dictionary and to determine a temperature change at the corresponding point in time of the acquisition. Advantageously, the thermal signal MRF dictionaries generated at blocks 408 and 420 may be generated on the fly during the temperature quantification and monitoring process using information from the previous time interval (or dynamic). As shown in FIG. 5, at a first temperature measurement time interval 510, a thermal signal MRF dictionary is generated 512 and a temperature change is determined 514 based on the MRF data acquired during the interval 510 and, as described above, the magnetization from the baseline measurement at interval 506. At a second temperature measurement time interval 516, a thermal signal MRF dictionary is generated 518 and a temperature change is determined 520 based on the MRF data acquired during the interval 518 and, as described above, the magnetization from the previous temperature measurement interval 510. At a third temperature measurement time interval 522, a thermal signal MRF dictionary is generated 524 and a temperature change is determined 526 based on the MRF data acquired during the interval 522 and, as described above, the magnetization from the previous temperature measurement interval 518. In the embodiment shown in FIG. 5, a temperature change may be determined for a time intervals of 219 time points (approximately 2.6 seconds of MRF data) by directly matching the acquired MRF data in the corresponding time interval to the thermal signal MRF dictionary. Accordingly, in some embodiments a temperature map may be generated approximately every 2.6 seconds and advantageously enables monitoring of the temperature every 2.4 seconds.

Returning to FIG. 4, at block 418 if the acquisition is complete, the process ends at block 422. As mentioned above, in some embodiments the method for temperature quantification using MRF may be used to monitor the temperature of tissues in a subject during thermal surgical procedures and guidance of thermal therapies. In such embodiments, the total length of the MRF acquisition (e.g., an MRFqRF acquisition as described above) may be determined based on the duration of the heating or cooling of the subject during the thermal surgical procedure or thermal therapy. In some embodiments, the thermal procedure, therapy or treatment may be stopped (manually or automatically) based on the determined temperature change and temperature map (blocks 410 and 412), for example, if the determined temperature falls above or below a predetermined threshold. In some embodiments, the thermal therapy or treatment may be modified (manually or automatically) based on the determined temperature change and temperature map (blocks 410 and 412), for example, if the determined temperature falls above or below a predetermined threshold.

Computer-executable instructions for magnetic resonance fingerprinting thermometry according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for temperature quantification using magnetic resonance fingerprinting (MRF) comprising:
   acquiring, using a magnetic resonance imaging (MRI) system, MRF data from a region of interest in a subject using an MRF pulse sequence with smoothly varying RF phase for MR resonant frequencies that is played out continuously; and
   for each of a plurality of temperature measurement time intervals during acquisition of the MRF data:
   generating a thermal signal MRF dictionary;
   comparing a set of MRF data associated with the temperature measurement time interval to the thermal signal MRF dictionary to determine a temperature change; and
   generating a quantitative map of the temperature change in the region of interest.

2. The method according to claim 1, wherein the plurality of temperature measurement time intervals includes a first temperature measurement time interval and a second temperature measurement time interval and generating the thermal signal MRF dictionary for the second temperature measurement time interval is based on at least information related to a determined temperature change for the first temperature measurement time interval.

3. The method according to claim 1, further comprising:
   for a baseline measurement time interval, comparing a set of the MRF data associated with the baseline measurement time interval to an MRF dictionary to determine at least one baseline quantitative parameter of the set of MRF data.

4. The method according to claim 3, wherein generating the thermal signal MRF dictionary is based on at least the at least one baseline quantitative parameter of the set of MRF data associated with the baseline measurement time interval.

5. The method according to claim 1, wherein the region of interest comprises a region of aqueous tissue.

6. The method according to claim 1, wherein the region of interest comprises a region of adipose tissue.

7. The method according to claim 1, wherein the RF pulse sequence is an MRF with quadratic RF phase (MRFqRF) pulse sequence.

8. The method according to claim 1, wherein the MRF pulse sequence is configured to be sensitive to $T_1$, $T_2$ and resonant frequency and the set of MRF data associated with the time measurement time interval includes at least one signal evolution.

9. The method according to claim 1, further comprising modifying a thermal treatment based on the determined temperature change.

10. A magnetic resonance imaging (MRI) system comprising:
    a magnet system configured to generate a polarizing magnetic field about at least a portion of a subject;
    a magnetic gradient system including a plurality of magnetic gradient coils configured to apply at least one magnetic gradient field to the polarizing magnetic field;
    a radio frequency (RF) system configured to apply an RF field to the subject and to receive magnetic resonance signals from the subject using a coil array; and
    a computer system programmed to:
    acquire MRF data from a region of interest in a subject using an MRF pulse sequence with smoothly varying RF phase for MR resonant frequencies that is played out continuously; and
    for each of a plurality of temperature measurement time intervals during acquisition of the MRF data:
    generate a thermal signal MRF dictionary;
    compare a set of MRF data associated with the temperature measurement time interval to the thermal signal MRF dictionary to determine a temperature change; and
    generate a quantitative map of the temperature change in the region of interest.

11. The MRI system according to claim 10, wherein the RF pulse sequence is an MRF with quadratic RF phase (MRFqRF) pulse sequence.

12. The MRI system according to claim 10, wherein the temperature change is associated with one of heating or cooling of a tissue in the region of interest of the subject.

* * * * *

UNITED STATES PATENT AND TRADEMARK OFFICE
CERTIFICATE OF CORRECTION

PATENT NO. : 11,519,987 B2
APPLICATION NO. : 17/301509
DATED : December 6, 2022
INVENTOR(S) : Kathryn Keenan et al.

It is certified that error appears in the above-identified patent and that said Letters Patent is hereby corrected as shown below:

In the Specification

Column 1, Line 23, "MM" should be --MRI--.

Column 1, Line 40, "MM" should be --MRI--.

Column 5, Line 45, "MM" should be --MRI--.

Column 5, Line 55, "MM" should be --MRI--.

Column 6, Line 16, "MM" should be --MRI--.

Column 7, Line 41, "MM" should be --MRI--.

Column 8, Line 61, "MM" should be --MRI--.

Column 8, Line 62, "MM" should be --MRI--.

Column 10, Line 17, "MM" should be --MRI--.

Column 14, Line 30, "MM" should be --MRI--.

Column 14, Line 36, "MM" should be --MRI--.

Column 15, Line 41, "MM" should be --MRI--.

Column 15, Line 47, "MM" should be --MRI--.

Signed and Sealed this
Fourteenth Day of February, 2023

Katherine Kelly Vidal
*Director of the United States Patent and Trademark Office*